(12) United States Patent
McCann et al.

(10) Patent No.: US 10,794,632 B2
(45) Date of Patent: Oct. 6, 2020

(54) VENTED COVER PLATE FOR AN ARRAY OF SYRINGES

(71) Applicant: TOLMAR Therapeutics, Inc., Fort Collins, CO (US)

(72) Inventors: Kevin Stuart McCann, Fort Collins, CO (US); Herbert Robert Brinkman, Fort Collins, CO (US); John Milton Downing, Fort Collins, CO (US)

(73) Assignee: TOLMAR THERAPEUTICS, INC., Fort Collins, CO (US)

( * ) Notice: Subject to any disclaimer, the term of this patent is extended or adjusted under 35 U.S.C. 154(b) by 37 days.

(21) Appl. No.: 16/073,835

(22) PCT Filed: Feb. 3, 2017

(86) PCT No.: PCT/US2017/016419
§ 371 (c)(1),
(2) Date: Jul. 30, 2018

(87) PCT Pub. No.: WO2017/136667
PCT Pub. Date: Aug. 10, 2017

(65) Prior Publication Data
US 2019/0041132 A1    Feb. 7, 2019

Related U.S. Application Data

(60) Provisional application No. 62/292,119, filed on Feb. 5, 2016.

(51) Int. Cl.
*F26B 5/06* (2006.01)
*F26B 25/00* (2006.01)
(Continued)

(52) U.S. Cl.
CPC .................. *F26B 5/06* (2013.01); *A61J 1/16* (2013.01); *A61J 1/2096* (2013.01); *A61J 3/02* (2013.01);
(Continued)

(58) Field of Classification Search
CPC combination set(s) only.
See application file for complete search history.

(56) References Cited

U.S. PATENT DOCUMENTS 3,454,178 A    7/1969    Bender et al.
3,810,469 A    5/1974    Hurschman
(Continued)

FOREIGN PATENT DOCUMENTS

EP    0664137    7/1995
EP    1617886    7/2015
(Continued)

OTHER PUBLICATIONS

International Search Report issued by the United States Patent and Trademark Office for International Patent Application No. PCT/US2017/016419, dated Apr. 27, 2017, 4 pages.
(Continued)

*Primary Examiner* — David J Laux
(74) *Attorney, Agent, or Firm* — Sheridan Ross P.C.

(57) ABSTRACT

A cover plate for use in lyophilization processes is provided. The cover plate includes a base portion and a plurality of protuberances which project from the base portion. The protuberances are adapted to fit in one or more delivery containers, such as syringe barrels. The cover plate permits the escape of vapor from the one or more delivery containers during a lyophilization process. In addition, the cover plate prevents the escape of lyophilizate from the one or more delivery containers during a lyophilization process. Vent features provided to provide enhanced and preferred venting operations during lyophilization processes.

19 Claims, 6 Drawing Sheets

(51) Int. Cl.

| | | |
|---|---|---|
| *A61J 3/02* | (2006.01) | |
| *A61M 5/178* | (2006.01) | |
| *A61J 1/16* | (2006.01) | |
| *A61J 1/20* | (2006.01) | |
| *A61K 38/09* | (2006.01) | |
| *A61M 5/00* | (2006.01) | |
| *B65D 51/16* | (2006.01) | |

(52) U.S. Cl.
CPC ............. *A61K 38/09* (2013.01); *A61M 5/008* (2013.01); *A61M 5/178* (2013.01); *B65D 51/16* (2013.01); *F26B 25/003* (2013.01)

(56) References Cited

U.S. PATENT DOCUMENTS

| | | | |
|---|---|---|---|
| 4,003,713 A | 1/1977 | Bowser | |
| 4,017,597 A | 4/1977 | Reynolds | |
| 4,060,911 A | 12/1977 | Weiler et al. | |
| 4,172,457 A | 10/1979 | Choksi et al. | |
| 4,250,139 A | 2/1981 | Luck et al. | |
| 4,286,389 A | 9/1981 | Ogle | |
| 4,306,357 A | 12/1981 | Villarejos | |
| 4,501,719 A | 2/1985 | Williams | |
| 4,521,975 A | 6/1985 | Bailey | |
| 4,729,208 A | 3/1988 | Galy et al. | |
| 4,758,230 A | 7/1988 | Rycroft | |
| 4,829,006 A | 5/1989 | Smith et al. | |
| 4,872,572 A | 10/1989 | Schrooten | |
| 4,874,381 A | 10/1989 | Vetter | |
| 4,878,597 A | 11/1989 | Haast | |
| 4,952,208 A | 8/1990 | Lix | |
| 5,000,737 A | 3/1991 | Free et al. | |
| 5,002,538 A | 3/1991 | Johnson | |
| 5,005,721 A * | 4/1991 | Jordan ................ | B01L 3/50853 220/23.4 |
| 5,080,649 A | 1/1992 | Vetter | |
| 5,184,450 A | 2/1993 | Galy et al. | |
| 5,234,529 A | 8/1993 | Johnson | |
| 5,279,608 A | 1/1994 | Cherif-Cheikh | |
| 5,320,603 A | 6/1994 | Vetter et al. | |
| 5,334,162 A | 8/1994 | Harris | |
| 5,352,756 A | 10/1994 | Meldal | |
| 5,354,562 A | 10/1994 | Platz et al. | |
| 5,478,946 A | 12/1995 | Murad et al. | |
| 5,519,984 A * | 5/1996 | Beussink ................ | B65B 3/003 53/324 |
| 5,542,935 A | 8/1996 | Unger et al. | |
| 5,595,760 A | 1/1997 | Cherif-Cheikh | |
| 5,596,814 A | 1/1997 | Zingle et al. | |
| 5,611,971 A | 3/1997 | Maedera et al. | |
| 5,653,693 A | 8/1997 | Miwa et al. | |
| 5,741,463 A | 4/1998 | Sanadi | |
| 5,770,559 A | 6/1998 | Manning et al. | |
| 5,779,668 A | 7/1998 | Grabenkort | |
| 5,803,284 A | 9/1998 | Grimard | |
| 5,807,345 A | 9/1998 | Grabenkort | |
| 5,819,964 A | 10/1998 | Grimard | |
| 5,882,603 A | 3/1999 | Taggart | |
| 5,900,422 A | 5/1999 | Ali | |
| 5,916,526 A | 6/1999 | Robbins | |
| 5,945,126 A | 8/1999 | Thanoo et al. | |
| 5,957,314 A | 9/1999 | Nishida et al. | |
| 5,958,714 A | 9/1999 | Gordon et al. | |
| 6,027,694 A | 2/2000 | Boulton et al. | |
| 6,033,603 A | 3/2000 | Lesczynski et al. | |
| 6,083,761 A | 7/2000 | Kedar et al. | |
| 6,087,324 A | 7/2000 | Igari et al. | |
| 6,090,925 A | 7/2000 | Woiszwillo et al. | |
| 6,096,562 A | 8/2000 | Bunn et al. | |
| 6,106,783 A * | 8/2000 | Gamble .............. | B01L 3/50825 422/553 |
| 6,136,273 A * | 10/2000 | Seguin ................ | B01L 3/50853 206/443 |
| 6,164,044 A | 12/2000 | Porfano et al. | |
| 6,189,292 B1 | 2/2001 | Odell et al. | |
| 6,199,297 B1 * | 3/2001 | Wisniewski ......... | B65D 51/241 206/439 |
| 6,221,854 B1 | 4/2001 | Radomsky | |
| 6,224,883 B1 | 5/2001 | Roskos et al. | |
| 6,241,949 B1 | 6/2001 | Kane | |
| 6,305,413 B1 | 10/2001 | Fischer et al. | |
| 6,340,589 B1 | 1/2002 | Turner et al. | |
| 6,436,351 B1 | 8/2002 | Gubernator et al. | |
| 6,455,005 B1 * | 9/2002 | Berray ................ | B01L 3/50853 215/247 |
| 6,566,144 B1 * | 5/2003 | Madril ..................... | F26B 5/06 436/174 |
| 6,722,054 B2 * | 4/2004 | Yarborough .............. | F26B 5/06 34/284 |
| 6,776,964 B1 * | 8/2004 | Wijnschenk ........ | B01L 3/50825 422/550 |
| 6,890,488 B2 * | 5/2005 | Mathus ............... | B01L 3/50853 422/550 |
| 6,907,679 B2 * | 6/2005 | Yarborough .......... | A61M 5/002 34/285 |
| 7,467,482 B2 | 12/2008 | Yarborough et al. | |
| D700,712 S * | 3/2014 | May ............................ | D24/224 |
| 9,003,676 B2 | 4/2015 | Yarborough et al. | |
| D804,050 S * | 11/2017 | Coulling ..................... | D24/224 |
| 9,931,635 B1 * | 4/2018 | Ho ...................... | B01L 3/50853 |
| 2001/0037091 A1 | 11/2001 | Wironen et al. | |
| 2001/0042317 A1 | 11/2001 | Yarborough et al. | |
| 2002/0055708 A1 | 5/2002 | Peterson | |
| 2002/0114737 A1 | 8/2002 | Mandril et al. | |
| 2005/0048575 A1 | 3/2005 | Coassin et al. | |
| 2015/0148752 A1 | 5/2015 | Yarborough et al. | |

FOREIGN PATENT DOCUMENTS

| | | |
|---|---|---|
| WO | WO 00/044641 | 8/2000 |
| WO | WO 01/047571 | 7/2001 |
| WO | WO 2006/045625 | 5/2006 |
| WO | WO 2012/042291 | 4/2012 |
| WO | WO 2017/136667 | 8/2017 |

OTHER PUBLICATIONS

Written Opinion issued by the United States Patent and Trademark Office for International Patent Application No. PCT/US2017/016419, dated Apr. 27, 2017, 8 pages.
Official Action (no English translation available) for Eurasian Patent Application No. 201891771, dated Oct. 10, 2019, 2 pages.
Extended European Search Report for European Patent Application No. 17748234.6, dated Aug. 28, 2019, 7 pages.
Official Action for Australia Patent Application No. 2004222346, dated Oct. 21, 2008 2 pages.
Notice of Acceptance for Australia Patent Application No. 2004222346, dated Feb. 8, 2010 3 pages.
Official Action for Australia Patent Application No. 2010201976, dated Apr. 11, 2011 3 pages.
Notice of Acceptance for Australia Patent Application No. 2010201976, dated Jul. 12, 2012 4 pages.
Official Action for Canada Patent Application No. 2,519,367, dated Apr. 30, 2008 3 pages.
Notice of Allowance for Canada Patent Application No. 2,519,367, dated Jul. 6, 2010 1 page.
International Search Report and Written Opinion for International (PCT) Patent Application No. PCT/US2004/007887, dated Jul. 16, 2004 12 pages.
International Preliminary Report on Patentability for International (PCT) Patent Application No. PCT/US2004/007887, dated Oct. 6, 2005 7 pages.
Official Action for European Patent Application No. 04757460.3, dated Jan. 19, 2009 3 pages.
Official Action for European Patent Application No. 04757460.3, dated Jan. 12, 2011 4 pages.
Official Action for European Patent Application No. 04757460.3, dated Feb. 4, 2014 4 pages.

(56) References Cited

OTHER PUBLICATIONS

Intention to Grant for European Patent Application No. 04757460.3, dated Mar. 11, 2015 5 pages.
Extended Search Report for European Patent Application No. 15178699.3, dated Jun. 14, 2016 6 pages.
Official Action for European Patent Application No. 15178699.3, dated Aug. 2, 2017 4 pages.
Intention to Grant for European Patent Application No. 15178699.3, dated Apr. 30, 2018 5 pages.
Official Action with English Translation for Japan Patent Application No. 2006-507209, dated Nov. 26, 2009 6 pages.
Official Action with English Translation for Japan Patent Application No. 2006-507209, dated Aug. 16, 2010 3 pages.
Notice of Allowance for Japan Patent Application No. 2006-507209, dated May 11, 2011 3 pages.
Official Action for U.S. Appl. No. 10/391,480, dated Apr. 7, 2004 12 pages.
Notice of Allowance for U.S. Appl. No. 10/391,480, dated Jul. 22, 2004 4 pages.
Notice of Allowance for U.S. Appl. No. 10/391,480, dated Feb. 4, 2005 4 pages.
Official Action for U.S. Appl. No. 11/099,919, dated Mar. 13, 2006 11 pages.
Official Action for U.S. Appl. No. 11/099,919, dated Aug. 22, 2006 10 pages.
Official Action for U.S. Appl. No. 11/099,919, dated Jan. 22, 2007 8 pages.
Official Action for U.S. Appl. No. 11/099,919, dated Jun. 14, 2007 8 pages.
Official Action for U.S. Appl. No. 11/099,919, dated Sep. 10, 2007 9 pages.
Official Action for U.S. Appl. No. 11/099,919, dated Nov. 21, 2007 9 pages.
Notice of Allowance for U.S. Appl. No. 11/099,919, dated Apr. 17, 2008 4 pages.
Official Action for U.S. Appl. No. 12/140,519, dated Oct. 15, 2010 22 pages.
Official Action for U.S. Appl. No. 12/140,519, dated May 26, 2011 26 pages.
Official Action for U.S. Appl. No. 12/140,519, dated Nov. 14, 2011 21 pages.
Official Action for U.S. Appl. No. 12/140,519, dated Sep. 4, 2012 19 pages.
Official Action for U.S. Appl. No. 12/140,519, dated Jun. 7, 2013 15 pages.
Official Action for U.S. Appl. No. 12/140,519, dated Nov. 18, 2013 16 pages.
Official Action for U.S. Appl. No. 12/140,519, dated Mar. 27, 2014 18 pages.
Notice of Allowance for U.S. Appl. No. 12/140,519, dated Dec. 5, 2014 9 pages.
Official Action for U.S. Appl. No. 14/590,779, dated Oct. 7, 2015 9 pages.
International Preliminary Report on Patentability for International (PCT) Patent Application No. PCT/US2017/016419, dated Aug. 16, 2018 10 pages.

\* cited by examiner

VENTED COVER PLATE FOR AN ARRAY OF SYRINGES

CROSS REFERENCE TO RELATED APPLICATIONS

This application is a national stage application under 35 U.S.C. of PCT Application No. PCT/US2017/016419 having an international filing date of Feb. 3, 2017, which designated the United States, which PCT application claimed the benefit of U.S. Provisional Patent Application Ser. No. 62/292,119, filed Feb. 5, 2016, the entire disclosure of both which are hereby incorporated by reference.

FIELD

The present disclosure relates generally to methods and systems for handling delivery containers, such as syringes. More specifically, the present disclosure relates to methods and systems for filling, sterilizing, and handling delivery containers, and for enabling certain process including, but not limited to, lyophilization of contents provided within one or more delivery containers.

BACKGROUND

Organic compounds, and more specifically pharmaceuticals, are generally more stable when they exist as a solid or powder than when they exist in solution. The shelf-life of a pharmaceutical stored in solution is generally shorter than the shelf-life of the pharmaceutical stored as a solid or powder. Since many pharmaceuticals are stored for extended periods of time before use, it is advantageous to have these pharmaceuticals remain active over the extended period of time. It is therefore desirable to store pharmaceuticals, over an extended period of time, as a solid or powder. This includes pharmaceuticals that are ultimately reconstituted as a solution before administration.

Lyophilization is routinely used in the preparation and storage of pharmaceuticals. In such applications, lyophilization is usually carried out by freezing a solution containing the pharmaceutical, followed by sublimation to provide the solid or powder essentially free of solvent. Lyophilization directly in a vial or ampule requires transfer of the reconstituted pharmaceutical from the vial or ampule to a syringe. As such, a syringe is especially useful for the lyophilization of an injectable medication since the medication is ultimately administered from the syringe. Lyophilization can be performed wherein the solution containing the pharmaceutical is lyophilized directly in a syringe. The lyophilized pharmaceutical (i.e., medication) can then be stored in the syringe wherein a diluent can be added to the syringe for reconstitution of the medication just prior to administration. The medication can then be administered from the syringe directly to the patient.

Even though lyophilization of a solution directly in a syringe is useful, there exist serious drawbacks. Lyophilization typically results in the solution "popping" or "bumping" when there is a residual amount of solvent remaining. This can result in solvent and pharmaceutical being displaced outside the syringe. In addition, the popping can result in cross contamination of adjacent syringes in the array. When lyophilization is performed directly in a syringe, a significant amount of solution containing the pharmaceutical can be displaced outside the syringe. Accordingly, one cannot be certain whether any such pharmaceutical has been displaced outside the syringe and therefore the amount of pharmaceutical remaining inside the syringe after lyophilization may not be sufficiently accurate or precise. Thus, the syringe and the contents therein must be recycled or discarded since the amount of pharmaceutical remaining in the syringe cannot be adequately ascertained for proper administration.

Alternatively, a pharmaceutical can be introduced into a syringe directly as a solid or powder. The syringe is usually filled with the pharmaceutical with the use of powder filling equipment.

Known cover plates for covering syringes and other containers during a lyophilization process generally comprise a planar portion and a plurality of projections or protuberances adapted to extend partially into an interior volume of a barrel prior to complete assembly of the syringe. Such devices and associated protuberances generally contemplate venting, at least in the sense that these devices are not intended to completely or securely seal the barrel of the syringe. Known devices comprise protuberances of a conical or frustoconical shape adapted to extending into a syringe barrel and contact or be supported by an open proximal end of the syringe barrel. Such devices fail to provide specific vent features. Frequently, such devices fail to enable venting, particularly if the devices have been subjected to autoclaving processes or excessive heat that warps the plastic or other material of the cover plate. In the event that such cover plates fail to properly vent or otherwise allow the escape of solvent or vapor, a "melt back" condition occurs, whereby incomplete sublimation of ice from the frozen product results in ice remaining in the lyophilization cake after drying and subsequent change (melt) of the cake from a solid to liquid state. In addition, in such a condition of failure to properly vent, full occlusion of the syringe barrel(s) provides an increase in pressure within the syringe barrel and/or syringe products and agent can be displaced. These circumstances will effectively ruin a filling or lyophilization process of the syringe and pose risks of cross-contamination of other syringes where product is blown or ejected from the syringe.

Known devices generally rely on an interaction between an inner diameter of a syringe barrel and an outer diameter of a protuberance of a cover plate to provide a temporary cover for syringes, tubes, or other devices during processing, such as a lyophilization process. In certain devices, weight is an important consideration as providing a cover plate with insufficient mass will enable the cover plate to move or be displaced too easily, while a cover plate with excessive mass may apply excessive force upon the syringe(s) and prevent venting or escape of lyophilized content, particularly if the device has been warped due to autoclaving, use, age, etc.

SUMMARY

There has been a long-felt and unmet need to provide a cover plate for use in a lyophilization process, and methods of use thereof, that comprises protuberances having venting structures and enable predictable and reliable venting of materials from a container during lyophilization processes while reliably covering, containing and protecting an internal volume of a container housing materials to be lyophilized.

Embodiments of the present disclosure provide a cover plate suitable for use to cover one or more delivery containers (e.g., syringes) during filling and lyophilization processes. The cover plates of the present disclosure include a lid region and one or more protuberances which project substantially perpendicularly from the lid region. The one or more protuberances are adapted to fit in one or more delivery containers. The cover plate permits the escape of vapor from the one or more delivery containers during the lyophilization process. In addition, the cover plate prevents the escape of lyophilizate from the one or more delivery containers during the lyophilization process.

Devices, methods and systems of the present disclosure contemplate a syringe nest provided within or in connection with a tub, such as Hypak® or Steripak® configuration of prepackaged syringes in a tub, as sold by Becton, Dickinson & Company or the TopPac® device available from Schott®.

Embodiments of the present disclosure also provide a system for lyophilizing a pharmaceutical solution, and ultimately the lyophilized product. The system includes one or more delivery containers suitable for containing the pharmaceutical solution. The system also includes a cover plate as shown and described herein.

Embodiments of the present disclosure also provide systems for lyophilizing a pharmaceutical solution including one or more apparatus and one or more delivery containers. At least one of the one or more delivery containers contains the pharmaceutical solution. The system also includes a cover plate of the present invention that covers the one or more delivery containers during the lyophilization process. Embodiments also include a delivery system comprising the at least one or more delivery containers containing the lyophilized pharmaceutical product or "lyophilizate" (e.g., after lyophilization is complete), and which also includes a cover plate of the present invention that covers the one or more delivery containers.

Embodiments of the present disclosure also provide methods for lyophilizing a solution. Such methods include, for example, depositing the solution in one or more delivery containers, covering the one or more delivery containers with a cover plate of the present invention, and lyophilizing the solution that includes the pharmaceutical. The cover plate allows pharmaceutical solutions to be lyophilized, and enables at least one of pressure, vapor, and gas to escape from the delivery container during a lyophilization process and while preventing cross contamination of adjacent syringes. In addition, the cover plate allows pharmaceutical solutions to be lyophilized while the amount of lyophilizate remaining inside the delivery containers is sufficiently ascertainable.

Embodiments of the present disclosure provide cover plates or restrictor plates used to cover one or more delivery containers during a lyophilization process. The cover plates of the present disclosure allow for the lyophilization of a solution in a delivery container whereby the solution and the lyophilizate remains inside the delivery container. During the lyophilization process employing the cover plate of the present invention, no significant amount of solution or lyophilizate is displaced from a delivery container. As such, the amount of lyophilizate remaining inside the delivery container is sufficiently ascertainable. In addition, cover plates of the present disclosure prevent cross-contamination of adjacent syringes in the array. In addition, the cover plates ensure that the venting during lyophilization is repeatedly and reliably sufficient such that meltback of the lyophilized product cakes due to occlusion of the syringes by the cover plate is substantially or entirely prevented.

As used herein, "lyophilization" refers to the removal of solvent from a frozen state by sublimation. Lyophilization is accomplished by freezing a solution below its melting point and then manipulating the temperature and pressure to provide sublimation. Precise control of temperature and pressure permits drying from the frozen state without product melt-back. In practical applications, the process is accelerated and more precisely controlled under reduced pressure conditions. Lyophilization or freeze drying is a process in which water is removed from a product after it is frozen and placed under a vacuum, allowing the ice to change directly from solid to vapor without passing through a liquid phase. The process generally consists of three separate, unique, and interdependent processes; freezing, primary drying (sublimation), and secondary drying (desorption).

In various embodiments of the present disclosure, a cover plate is provided comprising a base portion and at least one protuberance extending therefrom. The protuberances preferably comprise a conical or frustoconical shape with a first end proximal to the base portion and a second end opposite thereto. The first ends of the protuberances comprise a contact area for the cover plate where the contact plate is supported on or otherwise in contact with an open end of a syringe barrel. In preferred embodiments, the first ends of the protuberances comprise raised vent features wherein the raised vent features comprise support structures and/or contact areas for supporting the weight of the cover plate while allowing for one or more gaps or vents between an upper end of the syringe barrel(s) and the cover plate structure.

In various embodiments, one or more extensions are provided on a cover plate and wherein the extensions are not formed directly on the protuberance(s). Specifically, certain embodiments of the present disclosure contemplate the provision of stand-off features or extensions that are provided distally or spaced apart from the protuberances, and wherein the protuberances are prevented from fully occluding an open end of delivery containers.

In certain embodiments, the cover plate is provided with indicia to indicate which protuberances are intended to correspond to specific positions in a rack and/or delivery containers. For example, in certain embodiments, protuberances provided on a cover plate are provided with indicia (e.g. "A1, B5, C10," etc.), and wherein the indicia are indicative of a specific location, column, row, etc. of the protuberance on the cover plate. The indicia are intended to indicate which position on an associated rack that the protuberance is intended to be received by. Such indicia are useful, for example, where lyophilizate is captured on a protuberance and wherein it is then necessary to identify and discard the associated delivery container. The indicia provide for a means to readily identify the affected delivery container after the cover plate has been removed, manipulated, etc.

As used herein, "lyophilizate" generally refers to the solid, powder or granular material remaining after lyophilization. The solid, powder or granular material is essentially free of solvent.

In various embodiments, cover plates of the present disclosure can be used to lyophilize a solution containing a pharmaceutical in a delivery container. Any suitable pharmaceutical can be employed. Suitable pharmaceuticals include substances capable of prevention an infection systemically in an animal or human, or locally at the defect site, for example, antibacterial agents such as penicillin, cephalosporins, bacitracin, tetracycline, doxycycline, gentamycin, quinolines, neomycin, clindamycin, kanamycin, and metronidazole; anti-inflammatory agents such as hydrocortisone, and prednisone; antiparasitic agent such as quinacrine, chloroquine, and vidarbine; antifungal agents such as nystatin; antiviral agents such as acyclovir, ribarivin, and interferons; analgesic agents such as salicylic acid, acetaminophen, ibuprofen, naproxen, piroxicam, flurbiprofen, and morphine; local anesthetics such as cocaine, lidocaine, bupivacaine and benzocaine; immunogens (i.e., vaccines) for simulating antibodies against hepatitis, influenza, measles, rubella, tetanus, polio, and rabies; peptides such as an LH-RH agonist (e.g., leuprolide acetate), nafarelin, ganirelix, and goserelin. In one particular embodiment, the pharmaceutical is leuprolide, such as leuprolide acetate.

Other suitable pharmaceuticals include substances, or metabolic precursors thereof, which are capable of promoting growth and survival of cells and tissues or augmenting the functioning of cells. Suitable compounds capable of promoting growth and survival of cells and tissues or augmenting the functioning of cells include a nerve growth promoting substance, such as a ganglioside or a nerve growth factor; a hard or soft tissue growth promoting agent, such as fibronectin (FN), human growth hormone (HGH), a colony stimulating factor, bone morphogenic protein, platelet-derived growth factor (PDGF), insulin-derived growth factor (IGF-I, IGF-II), transforming growth factor-alpha (TGF-α), transforming growth factor-β (TGF-β), epidermal growth factor (EGF), fibroblast growth factor (FGF), interleukin-1 (IL-1), and prostaglandins such as PGE1, PGE2 and PGD2; and an osteoinductive agent or bone growth promoting substance such a bone chips or demineralized bone material. Suitable pharmaceutical agents include antineoplastic agents such as methotrexate, 5-fluouracil, adriamycin, vinblastine, cisplatin, tumor-specific antibodies conjugated to toxins, and tumor necrosis factor.

Other suitable pharmaceuticals include hormones such as progesterone, testosterone, follicle stimulating hormone (FSH) (used for birth control and fertility-enhancement), insulin, and somatotropins; antihistamines such as diphenhydramine and chlorphencramine; cardiovascular agents such as digitalis, nitroglycerine, papaverine and streptokinase; anti-ulcer agents such as cimetidine hydrochloride, and isopropamide iodide; bronchodilators such as metaprotemal sulfate and aminophylline; vasodilators such as theophylline, niacin and minoxidil; central nervous system agents such as tranquilizers, β-adrenergic blocking agents, and dopamine; antipsychotic agents such as risperidone and olanzapine; narcotic antagonists such as naltrexone, naloxone and buprenorphine.

Additional suitable pharmaceuticals are provided in U.S. Pat. No. 5,234,529, the disclosure of which is incorporated by reference herein. The pharmaceutical can optionally include a suitable excipient. Suitable excipients include ionic and non-ionic (amphoteric) surfactants (e.g., polysorbates, cremophores and tyloxopols), bulking agents (e.g., sodium phosphates, potassium phosphates, citric acid, tartaric acid, gelatins, and carbohydrates such as dextrose, mannitol and dextran), and lyoprotectants (e.g., glucose, catalase, maltose, maltotriose and maltohexose).

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of the teachings of this disclosure invention and is not meant to limit the inventive concepts disclosed herein.

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Cover plates of the present disclosure can be constructed from any suitable material. The material, or combination of materials, is preferably resistant to the temperature and pressure changes that exist during the lyophilization process. In addition, the material is preferably durable, inexpensive, and reusable. Suitable materials include, but are not limited to plastics, TEFLON®, rubber, fiberglass, glass, and any combination thereof. Plastic is one preferable material for making the cover plate, as it is relatively light, durable, easy to use and relatively inexpensive.

Figure 1:
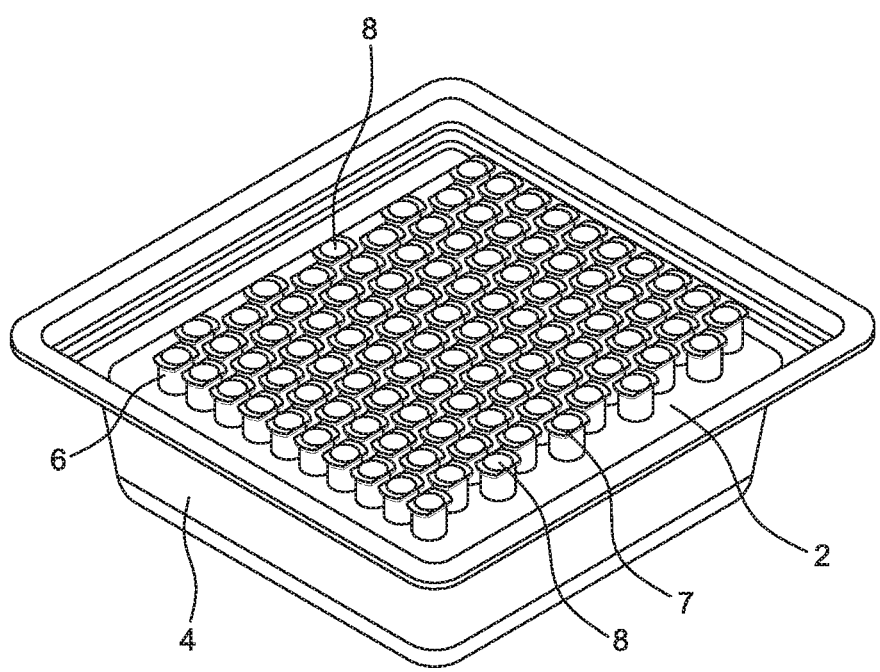
FIG. 1 is a front perspective view of a syringe nest and associated tub.

As shown in FIG. 1, a syringe nest or rack 2 is provided within a tub 4. The syringe nest 2 comprises a plurality of wells 6 for receiving syringes 7, the syringes 7 comprising an open end 8 of a barrel portion. The open end 8 comprises an opening that is generally exposed and adapted to receive a plunger rod (for example) after filling and/or sterilization process of the syringes are complete. FIG. 1 depicts a syringe nest 2 with a plurality of syringes 7 disposed therein and wherein the open ends 8 of the syringes 7 are exposed to an outside environment.

Figure 2:
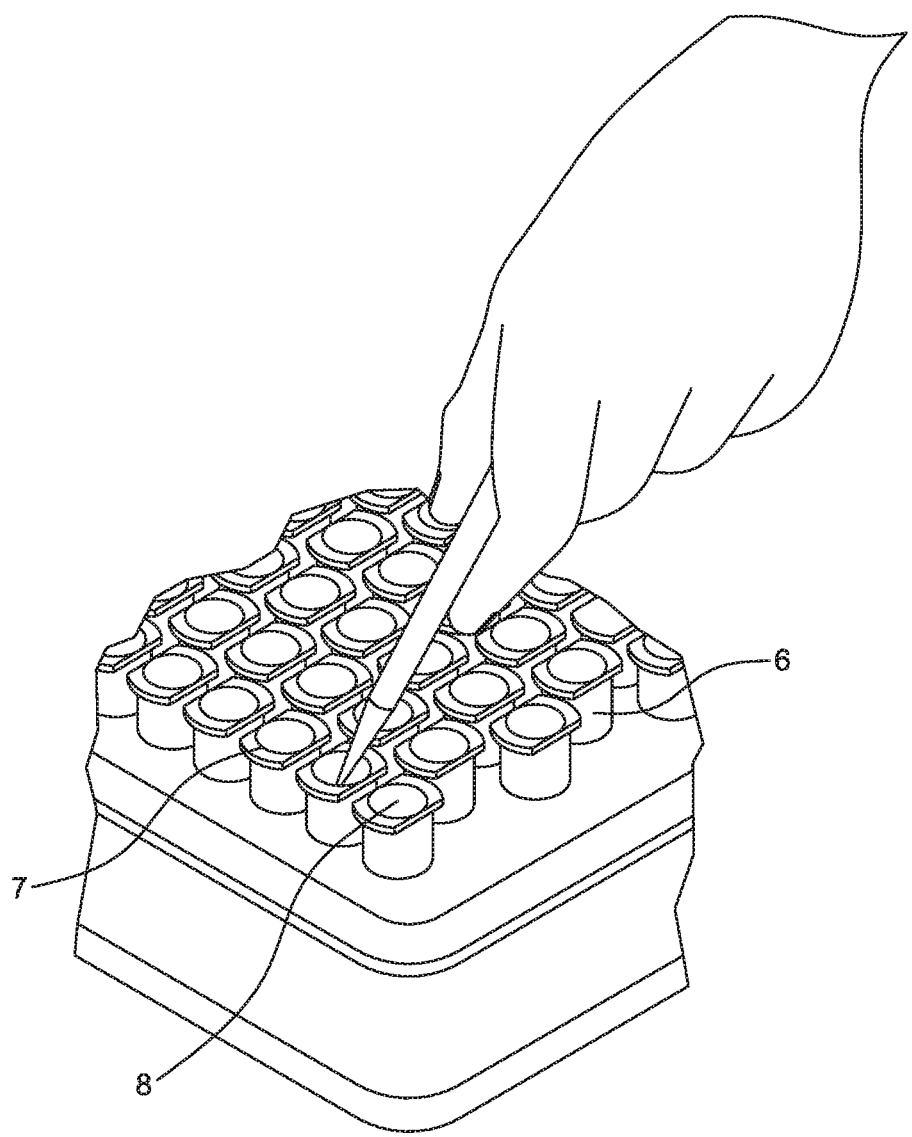
FIG. 2 is a detailed perspective view of a syringe nest and associated tub.

FIG. 2 is a detailed perspective view of the system of FIG. 1, wherein syringes 7 comprise an open end 8. As shown, the open ends 8 allow access to an interior portion of a syringe barrel for various operations including, but not limited to, filling and lyophilization.

Figure 3:
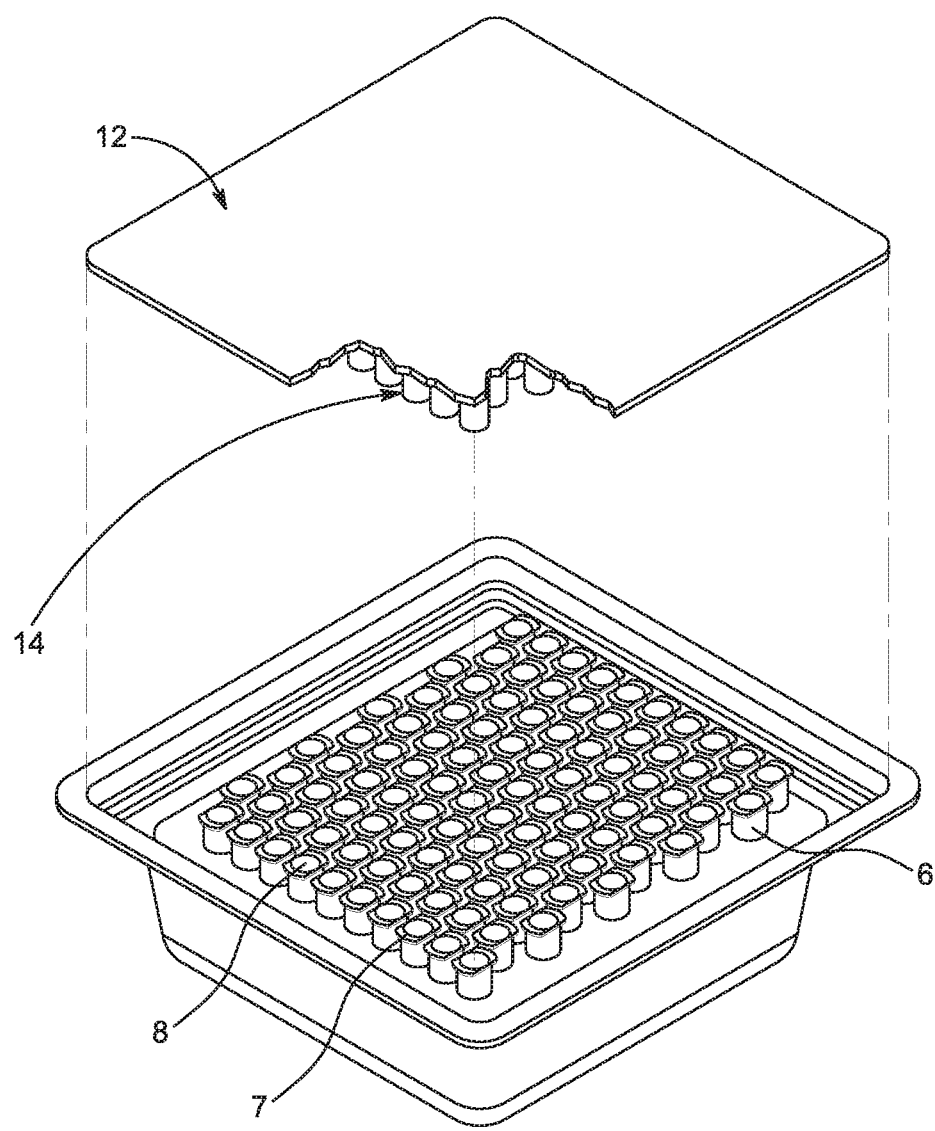
FIG. 3 is a perspective view of a tub, syringe nest and cover plate.

FIG. 3 is a perspective view of a syringe storage system or assembly comprising a syringe nest or rack 2 in combination with a tub 4 and a cover plate 12. The cover plate 12 comprises a plurality of protuberances 14. The number and geometry of the protuberances 14 preferably correspond to the number of wells provided in the syringe nest 2. The cover plate 12, as shown and described in more detail herein, generally comprises a cover plate for placing in contact and communication with the syringe nest 2 and associated syringes. In various embodiments, the cover plate 12 comprises a device that is adapted to rest on the syringe nest 2 and/or the plurality of syringes. In other words, the plate is not fastened or securely connected to the syringes or the syringe nest, but rests on the syringes or syringe nest under the force of gravity. In alternative embodiments, however, a restrictor plate is provided comprising one or more fasteners to securely connect the plate to the syringe nest 2 or the tub 4.

Figure 4:
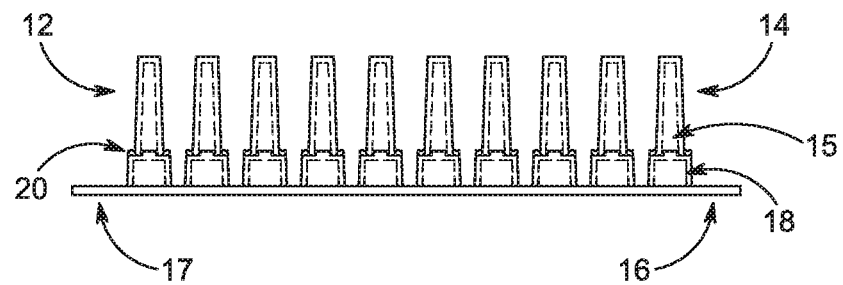
FIG. 4 is a side elevation view of a cover plate according to one embodiment of the present disclosure.

FIG. 4 is a front elevation view of a cover plate 12 in accordance with one embodiment of the present disclosure. As shown, the cover plate 12 comprises a plurality of protuberances 14 extending from a base portion 16. The base portion 16 preferably comprises a rectangular and substantially planar base. The base portion 16 extends outwardly beyond the protuberances 14 to provide a flange 17 extending around a perimeter or a portion of the perimeter of the base portion 16. The protuberances further comprise a first portion 15 and a second portion 18. The first portions 15 and the second portions 18 of the protuberances preferably comprise frustoconical members wherein the smallest outer diameter of the second portions 18 is greater than the largest outer diameter of the first portions 15. The first portions 15 are provided to extend at least partially into a delivery container, such as a syringe barrel. The second portions 18 are provided and adapted to provide support and rest above an open end of the delivery container at least when the plate 12 is provided in a first position of use. The second portions 18 comprise extensions 20 that are preferably distributed about a circumference of the second portion 18 and/or first portion 15. In the embodiment of FIG. 4, the extensions 20 comprise rectangular or blocked shaped extensions, giving the second portions a turret-like appearance, and wherein distal ends of the extensions 20 comprise support surfaces for resting on a proximal end of a delivery container, such as a syringe barrel. When provided in a position of use, with the distal ends of the extensions 20 resting on the proximal ends of the delivery container(s), the spacing or gaps between the extensions comprise gaps or vents 30 (see FIG. 6) to allow gas and vapor to escape from the delivery container(s) during a lyophilization procedure, for example. Although the extensions provided in FIG. 4 comprise a plurality of rectangular extensions extending from the second portions 18 and along an outer surface of the first portions 15, it will be recognized that the extensions 20 may comprise any number of shapes, geometries, orientations, positions, etc. and still constitute features within the scope of the present disclosure. It will further be recognized that a void space, or spacing between the extensions 20 provide vent features or fluid flow paths to allow gas to flow between and/or around the extensions 20 and therefore escape a delivery container in which the gas is stored or formed. Accordingly, the extensions 20 are contemplated as comprising extensions of any shape, size, position, etc.

In preferred embodiments, a plurality of extensions 20 are provided that are evenly spaced about a circumference of the protuberance 14 such that each of the extensions are adapted to rest on an open end of a delivery container and each protuberance 14 is evenly supported on or in the delivery container. The extensions 20 extend from an outer surface of the protuberances and provide an irregular shape to the outer surface of the protuberances. In some embodiments, the protuberances 14 comprise triangular, circular, irregular, or other extensions with at least one gap provided between extensions. In one alternative embodiment, a protuberance is provided with one or more flutes or recesses such that the protuberance rests in and/or on a delivery container and vapor or gas is allowed to escape from the delivery container and the restrictor plate through the flute(s) or recess(es). The flutes are contemplated as comprising slots or depressions in the sidewall(s) of the protuberances, wherein the sidewall of the protuberances contact the syringe barrel, and the flutes extend above and below the rim or lip of the syringe barrel to allow for egress of lyophilized contents. The flutes may be of various shape including, for example, oval, circular, tear-drop shaped, etc.

Figure 5:
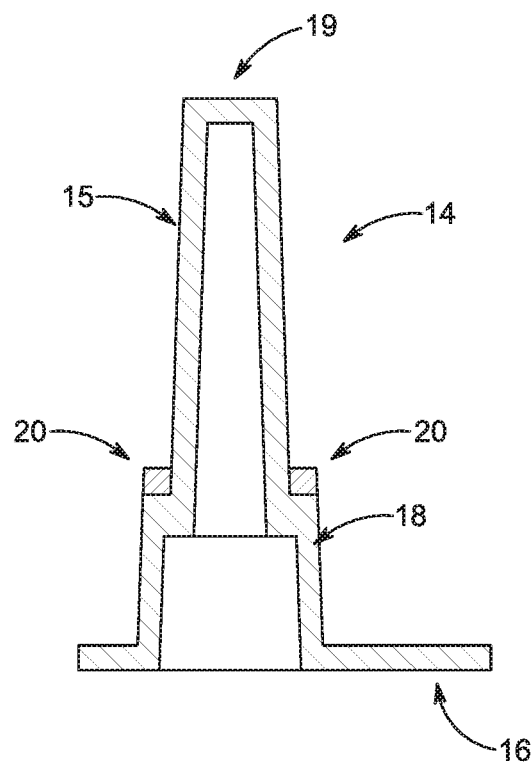
FIG. 5 is a cross-sectional elevation view of a cover plate according to the embodiment of FIG. 5.

FIG. 5 is a cross-sectional elevation view of a single protuberance 14 extending from a base portion 16 of a cover plate 12, and taken through a center-line of the protuberance 14. As shown, the protuberance 14 comprises a first portion 15 and a second portion 18. At least a portion of the first portion 15 is adapted to extend into an internal volume of a delivery container. The external surface and distal end 19 of the protuberance 14 serve to cover and trap lyophilizate within an interior volume of a delivery container, while the second portion 18 and extensions 20 allow for the escape of gas and material necessary to the completion of a lyophilization process, or similar process.

In various embodiments, the cover plate comprises between 1 to about 300, 1 to about 200, 50 to about 150 or, preferably, about 75 to about 125 protuberances 14. As shown and described, the protuberances serve as a non air-tight stopper, plug or cap over a delivery container, thereby preventing the escape of lyophilizate from the delivery container during lyophilization. In addition, suitable protuberances can catch lyophilizate that contacts the protuberance 14 during lyophilization. Accordingly, a suitable protuberance 14 prevents lyophilizate from one delivery container from being introduced into another delivery container during lyophilization, thereby contaminating the contents of one delivery container with the contents of another delivery container. In addition, a suitable protuberance 14 permits lyophilization to proceed by allowing vapor to pass from the interior of the delivery container to the exterior of the delivery container during lyophilization.

The protuberances 14 preferably fit within an opening 8 of the delivery container 7 to prevent the escape of lyophilizate from the delivery container 7 and to allow vapor to pass from the interior of the delivery container 7 to the exterior of the delivery container 7 during lyophilization. As such, the protuberance 14 can have any suitable shape. The protuberance 14 can assume any suitable shape which generally corresponds with or is received within the shape of the opening 8 of the delivery container 7, so long as the protuberance 14 cooperates with the opening 8 of the delivery container 7. The protuberance 14 may be shaped in any suitable manner provided it caps or plugs the opening 8 of the delivery container 7 and permits the passage of vapor during lyophilization. As such, the shape of the protuberance 14 can depend upon the shape of the opening 8 of the delivery container 7.

Specifically, the protuberance 14 can be spherically shaped, conically shaped, frustoconically shaped or cylindrically shaped. In addition, the cylindrically shaped protuberance 14 can be tapered. The protuberance 14 can be tapered from a first end of the protuberance proximal to the base portion 16 to a second end of the protuberance provided distally therefrom and adapted to be inserted into a delivery container. Alternatively, the protuberance(s) 14 can be tapered from the lowest point vertically on the protuberance 14 after the cover plate 12 is placed atop a tub.

In various embodiments, the protuberance(s) comprise a length as small as hundredths of an inch or as large as several inches, depending upon the size and depth of delivery containers. Generally, the longer the protuberances 14, the more firmly in place they will keep the cover plate 12 relative to the delivery containers 8 during lyophilization. In one embodiment, a length of each protuberance 14 is between about 1.0 inch and about 2.0 inches, and more preferably is about 1.4 inches to about 1.6 inches.

The suitable length of the protuberance 14 can typically depend upon the length of the delivery containers and the amount of contents in the delivery containers. Preferably, the suitable length of the protuberance 14 will minimize or lessen the occurrence of the contents of the delivery containers 7 from obtaining sufficient kinetic energy to be ejected out of the delivery containers 7. The suitable length of the protuberance 14 will minimize or lessen this occurrence by extending within about 0.5 inch, within about 0.25 inch, or within about 0.1 inch of the contents of the delivery containers 8.

In various embodiments, the spacing and positioning of the protuberances 14 are provided to correspond to the spacing and positioning of wells or delivery containers 7 to which the cover plate 12 is designed to cooperate or mate with. Accordingly, this spacing or positioning can be varied. In one embodiment, a distance between axial centers of adjacent protuberances in the same row, can be about 0.5 inch to about 0.9 inch, and more specifically can be about 0.6 inch to about 0.7 inch. The distance horizontally between axial centers of the nearest two protuberances 30 in adjacent rows, can be about 0.25 inch to about 0.5 inch, and more specifically can be about 0.3 inch to about 0.4 inch. The distance horizontally between axial centers of the nearest two protuberances 30 in adjacent rows, can be about 0.4 inch to about 0.9 inch, and more specifically can be about 0.6 inch to about 0.7 inch.

Figure 6:
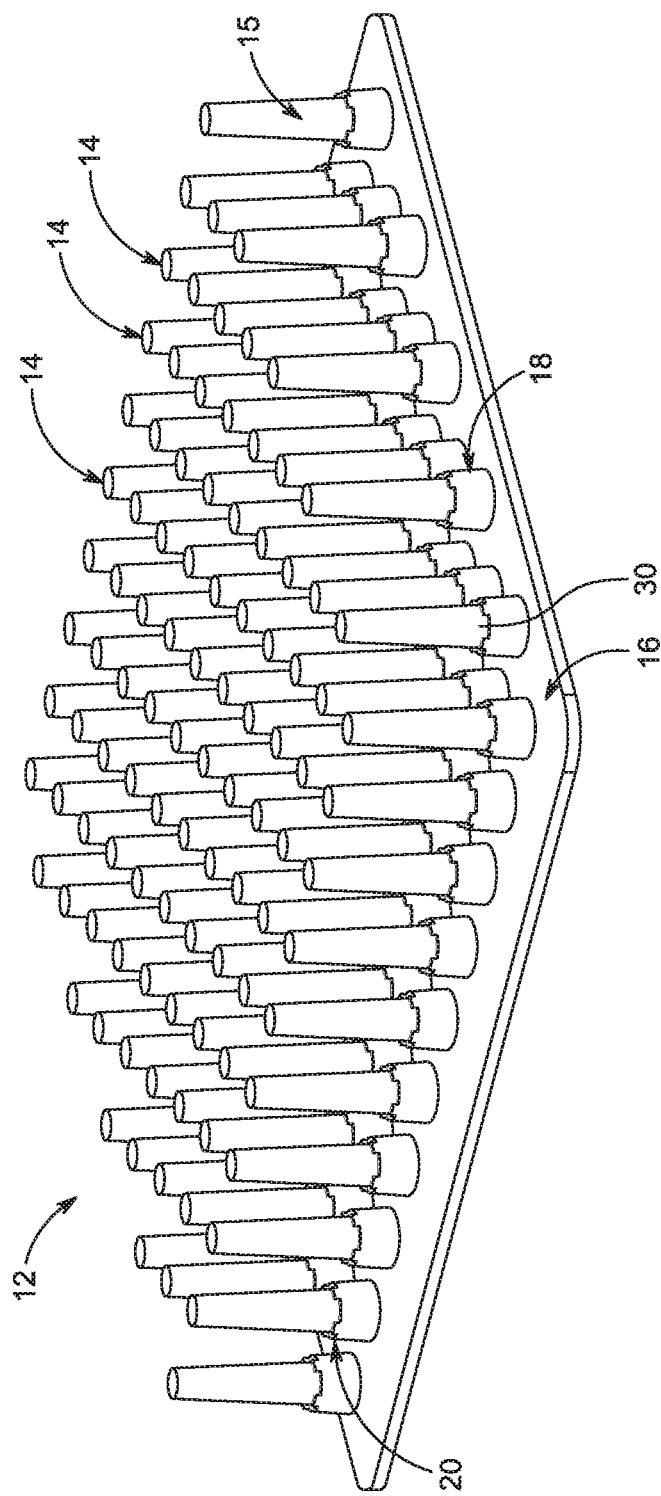
FIG. 6 is a perspective view of a cover plate in accordance with one embodiment of the present disclosure.

As shown in FIG. 6, each of the protuberances 14 comprise a plurality of extensions 20 distributed about a circumference of the protuberance. In the depicted embodiment, four extensions 20 are provided on each protuberance 14. It will be recognized, however, that the number, type, and/or location of the extensions may be various without deviating from the scope and spirit of the present invention. The cover plate 12 of the present disclosure provides a reliable system and method for venting during a lyophilization procedure, wherein the cover plate's ability to vent contents housed within a delivery container is not substantially altered or affected by age, sterilization processes, and other factors known to affect the size, shape and integrity of a cover plate. It is contemplated that the extensions 20 as shown and described herein provide a novel arrangement for providing desired venting properties, and wherein such venting properties are not substantially degraded by minor changes in the size, shape, hardness, etc. of the cover plate, which are known to vary over time in existing devices. The extensions 20 are distributed and spaced-apart to provide vents 30 between adjacent extensions 20.

Figure 7:
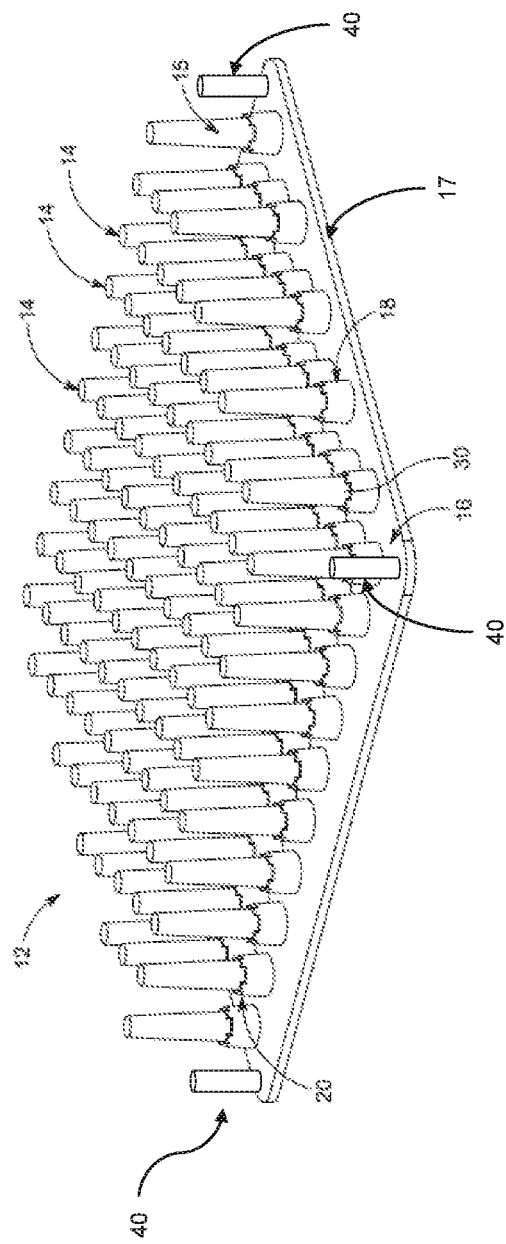
FIG. 7 is a perspective view of a cover plate in accordance with one embodiment of the present disclosure.

FIG. 7 is a perspective view of a cover plate according to one embodiment of the present disclosure. As shown, the cover plate 12 comprises a plurality of protuberances 14 extending from a base portion 16. The base portion 16 preferably comprises a rectangular and substantially planar base. The base portion 16 extends outwardly beyond the protuberances 14 to provide a flange extending around a perimeter or a portion of the perimeter of the base portion 16. The cover plate 12 of FIG. 7 further comprises a plurality of extensions in the form of posts 40 provided on the flange 17. The posts 40 are operable to provide a stand-off height between the cover plate 12 and a rack and/or tub (not shown in FIG. 7). Specifically, the posts 40 comprise a height with a first end provided on the flange 17 and a second end comprising a free end. The second end is operable to contact at least one of a rack and a tub, and limit an amount, distance, or extent in which the protuberances 14 are allowed to extend into delivery containers when the cover plate is applied or positioned on the delivery containers. When the second end of the posts 40 is provided in contact with the tub and/or rack, a stand-off height is provided wherein the protuberances 14 are prevented from fulling extending into and therefore occluding the delivery containers. Accordingly, an annular gap is provided between each of the protuberances and a corresponding delivery container. The annular gaps serve as vent features to allow for escape of matter during lyophilization and sublimation. As shown, the posts 40 are provided at each of the four corners of the cover plate 12 to provide stability. It will be recognized, however, that the posts and similar stand-off features may be provided at various different positions on the plate 12. Additionally, although four posts 40 are shown in FIG. 7, various numbers of posts are contemplated in alternative embodiments of the present disclosure.

Delivery containers as disclosed and described herein may include any receptacle in which a pharmaceutical can be lyophilized. Specifically, the delivery containers may comprise ampules, vials, or syringes. Syringes are specifically suitable for lyophilizing pharmaceuticals whose ultimate use will be administration from a syringe. The pharmaceutical can be reconstituted, if necessary, in the syringe in which the pharmaceutical was lyophilized. Accordingly, syringes are especially suitable for lyophilizing an injectable pharmaceutical (i.e., medication), since the medication is ultimately administered from the syringe.

The syringe can be manufactured from any suitable material. Suitable materials are those materials that are resistant to the temperature and pressure changes that exist during the lyophilization process. The material can be durable and inexpensive. Suitable materials include plastics, glass, and any combination thereof.

Specifically, the syringe can be manufactured from plastic. Plastic syringes are generally stronger than glass syringes. The increased strength of plastic results in a more durable syringe. The increased durability allows for a safer syringe as a plastic syringe will not break as easily upon administration as compared to a glass syringe. As such, fewer health care professionals will become injured while reconstituting and administering injectable medications in a plastic syringe as compared to a glass syringe.

Due to the increased strength of plastic syringes, the bore size of plastic syringes is routinely larger than those of comparable glass syringes, thereby decreasing the force required to use the plastic syringe. This is especially useful when reconstituting an injectable medication with a very viscous diluent or for syringe-to-syringe reconstitution. See, U.S. patent application Ser. No. 09/405,463 filed on Sep. 24, 1999.

The syringe can be disposable or can be reusable. Disposable syringes are commercially available and are usually constructed from plastic or glass. Disposable syringes are popular due to their convenience and because they are relatively inexpensive. A suitable disposable plastic syringe of the present invention is manufactured by Becton Dickinson & Company in what is known as a "Hypak" configuration and is disclosed in U.S. Pat. No. 4,758,230, for example.

The solution containing the pharmaceutical can be cooled to a frozen solid prior to lyophilization. The solution can be cooled by any suitable cooling means (e.g., convention, conduction or radiation). Specifically, the solution can be cooled by convection.

After the solution is cooled to a frozen solid, a partial vacuum is applied to the lyophilizing apparatus to provide a partial vacuum within the lyophilizing apparatus (i.e., within the inside of the delivery container and on the outside of the delivery container). The partial vacuum can be applied to the solution, in the frozen state, until essentially all of the solvent is removed (i.e., to dryness).

After lyophilization is completed, the tub can be removed from the lyophilization apparatus. The cover plate 12 can be removed from the delivery container 7 and examined for any retained lyophilizate. If the protuberances 14 of the cover plate 12 contains any lyophilizate, each delivery container 8 from which the lyophilizate originated can be discarded or recycled and the lyophilizate can be recycled or discarded. If any pharmaceutical leaves a delivery container and is captured on the restrictor plate, the amount of lyophilized pharmaceutical remaining in the delivery container is unknown. Thus, any delivery container losing any lyophilizate captured by the cover plate can be discarded or recycled. Accordingly, the cover plate is removed from on top of the delivery container and examined for any retained lyophilizate. If the cover plate contains any lyophilizate, each delivery container from which the lyophilizate originated can be discarded or recycled.

After lyophilization, the opening 8 of any undiscarded delivery container 7 can be sealed for storage. The delivery container 7 can be sealed with any suitable sealing device known for sealing delivery containers 7. Where the delivery container 7 is a syringe, the proximal opening of the syringe barrel can be sealed with the plunger of the syringe.

The embodiment of FIG. 7 depicts a cover plate 12 comprising a plurality of posts 40 and a plurality of extensions 20 provided on the protuberances 14. However, in at least some embodiments, it is contemplated that the posts 40 comprise features that obviate the need for the depicted extensions 20.

In various embodiments, methods of performing lyophilization are provided. In certain embodiments, methods of lyophilization comprise providing a cover plate with a plurality of protuberances as shown and described herein.

For illustrative purposes, a method of lyophilization according to one embodiment of the present disclosure is provided as follows: lyophilization of leuprolide acetate is achieved by providing a solution containing leuprolide acetate in a solvent, e.g. water, prepared by mixing leuprolide acetate in water until dissolved. A tub of syringes is opened so the opening of the proximal end of each syringe is exposed. Leuprolide acetate solution with approximately 7.5 mg of leuprolide acetate is filled into each syringe by means of a pipette (for example) through the opening of the proximal end of each syringe. This procedure is repeated with three additional tubs of syringes into which leuprolide acetate solution with approximately 22.5, 30, or 45 mg of leuprolide acetate is filled. When the syringes in a tub are filled with the leuprolide acetate solution, the tub containing the plurality of syringes is placed on a shelf of a lyophilizing apparatus. The syringes are then covered with a cover plate (see FIG. 6, item 12, for example). The shelf of the lyophilizing apparatus includes a refrigerant circulating within the shelf to control temperature and to facilitate a conductive heat transfer between the shelf and tub. The temperature of the shelf is reduced to approximately −50° C. until the solution in each syringe is frozen well below 0° C. by radiant and/or convectant cooling. A vacuum is applied to the chamber and the shelf temperature is slowly raised to room temperature until the water in the syringes is removed by sublimation, wherein sublimated fluid is allowed to escape through the one or more vent features provided by the extensions provided on each protuberance of the cover plate. The result is a lyophilized powder in each syringe of approximately 7.5, 22.5, 30 or 45 milligrams. One of ordinary skill in the art will recognize that processes of the present disclosure, including the aforementioned process, may be varied by altering the amounts and concentrations provided. For example, the resultant quantity of lyophilized powder may be varied providing a larger or smaller initial volume of the of the leuprolide acetate solution. Additionally, the initial concentration of the solution of leuprolide acetate in water may be varied. Variations of the quantities noted above may be provided to produce a different resultant quantity of lyophilized powder or to provide the same resultant quantity using different inputs while performing essentially the same method steps.

The tub is removed from the lyophilizing apparatus. The cover plate is removed from the opening of the syringes. Each area of the covering plate is examined for captured lyophilizate and the syringes from which any such captured lyophilizate came are discarded. Plunger tips are installed into the opening of the proximal end of the syringes, and plunger rods are screwed into the corresponding plunger tips. The syringes are now ready for reconstitution.

In the following example, lyophilization experiments were conducted to determine the effects of syringe occlusion: syringes were intentionally occluded to observe effects of restricting water vapor flow from the syringe during lyophilization. Syringes were occluded by creating a vent through stoppered syringes using ⅝" needles of varied gauges. Specifically, partial occlusion was accomplished by piercing syringe stoppers with a 27 gauge needle (0.21 mm nominal ID), a 20 gauge needle (0.63 mm nominal ID), and a 16 gauge needle (1.2 mm nominal ID).

The syringes were filled with a leuprolide acetate solution by hand using a micropipette and were weight checked. The syringes were loaded into tubs and were subjected to a lyophilization cycle such as those described herein. Meltback or failed lyophilization was observed in syringes that were occluded and lacked sufficient venting. Specifically, it was observed that it is desirable to have a vent or opening of at least approximately 1.0 mm$^2$ to facilitate proper lyophilization. It will be recognized, however, that the present disclosure is not limited to any particular minimum area for a vent feature. In certain embodiments, however, it is preferable to provide at least approximately 1.0 mm$^2$ of vent area between an otherwise covered or closed end of a delivery container that is subjected to a lyophilization process.

The results of this experiment showed that the degree of occlusion for the syringes impacts lyophilization. When vent size was varied from 0.21 mm (27G) to 1.2 mm (16G) using hypodermic needles, the degree of success of lyophilization was also varied. Syringes with 0.21 mm vents showed little if any lyophilization, while those with 1.2 mm vents dried normally.

While various embodiments of the present invention have been described in detail, it is apparent that modifications and alterations of those embodiments will occur to those skilled in the art. However, it is to be expressly understood that such modifications and alterations are within the scope and spirit of the present invention. Further, the invention(s) described herein are capable of other embodiments and of being practiced or of being carried out in various ways. In addition, it is to be understood that the phraseology and terminology used herein is for the purposes of description and should not be regarded as limiting. The use of "including," "comprising," or "adding" and variations thereof herein are meant to encompass the items listed thereafter and equivalents thereof, as well as, additional items.

What is claimed is:

1. A cover plate adapted for communication with a plurality of delivery containers during a lyophilization process, the cover plate comprising:
    a base portion comprising a length and a width;
    a plurality of protuberances extending from the base portion and distributed along at least one of the length and the width of the base portion;
    each of the plurality of protuberances adapted to extend at least partially into a delivery container;
    the cover plate further comprising a plurality of extensions in the form of posts or stand-off features spaced apart from the protuberances, and wherein the plurality of extensions are operable to provide a stand-off height and limit an amount, distance or extent in which the protuberances extend into delivery containers, and wherein free ends of the posts or stand-off features are operable to contact at least one of a rack and a tub and limit an amount, distance or extent in which the protuberances are allowed to extend into the delivery containers when the cover plate is applied or positioned on the delivery containers thus preventing the protuberances from fully extending into the delivery containers;
    wherein at least one vent feature is provided by the stand-off height to allow at least one of a gas, a vapor, and a fluid to flow therethrough;
    and wherein the cover plate substantially prevents the escape of a lyophilizate from delivery containers during a lyophilization process.

2. The cover plate of claim 1, wherein each of the plurality of protuberances comprises a frustoconical member.

3. The cover plate of claim 1, wherein the protuberances are provided in an array.

4. The cover plate of claim 1, wherein the extensions are provided on the base portion.

5. The cover plate of claim 1, wherein the base portion comprises four corners and the extensions are provided at each of the four corners of the base portion.

6. The cover plate of claim 1, wherein the at least one vent feature comprises an annular gap between at least one of the plurality of protuberances and a delivery container.

7. The cover plate of claim 1, wherein at least some of the plurality of extensions are provided in contact with at least one of a rack and a tub.

8. The cover plate of claim 1, wherein the plurality of extensions comprises four extensions.

9. A system for handling a plurality of delivery containers during a lyophilization process, the system comprising:
    a tub;
    a rack operable to suspend a plurality of containers in an upright position such that an opening of each of the containers faces toward a top of the tub;
    a cover plate comprising a plurality of protuberances distributed along at least one of a length and a width of the cover plate, wherein each of the plurality of protuberances is adapted to extend at least partially into a container;
    wherein the cover plate comprises a plurality of extensions in the form of posts or stand-off features;
    wherein the extensions are operable to contact at least one of the tub and the rack and provide a stand-off height of the rack to prevent the protuberances from occluding the containers;
    wherein free ends of the extensions are operable to contact at least one of a rack and a tub and limit an amount, distance or extent in which the protuberances are allowed to extend into the containers when the cover plate is applied or positioned proximal to the containers thus preventing the protuberances from fully extending into the containers;
    and wherein the extensions provide a vent feature between the containers and the cover plate that substantially prevents the escape of a lyophilizate from the one or more containers during a lyophilization process.

10. The system of claim 9, wherein the rack comprises a flange and wherein the flange comprises a contact surface for placing the rack in contact with the tub.

11. The system of claim 10, wherein the extensions are operable to contact the flange of the rack.

12. The system of claim 9, wherein each of the plurality of protuberances comprises a frustoconical member.

13. The system of claim 9, wherein the containers comprise syringe barrels.

14. The system of claim 9, wherein the delivery containers contain leuprolide acetate.

15. The system of claim 9, wherein the plurality of extensions comprises four extensions.

16. A method for lyophilizing a solution containing leuprolide acetate, comprising:
    providing a cover plate comprising a base portion comprising a length and a width; a plurality of protuberances extending from the base portion and distributed along at least one of the length and the width of the base portion; each of the plurality of protuberances adapted to extend at least partially into a delivery container;
    wherein the cover plate comprises a plurality of extensions in the form of posts or stand-off features that are operable to provide a stand-off height and limit an amount, distance or extent in which the protuberances extend into delivery containers;
    wherein free ends of the extensions are operable to contact at least one of a rack and a tub and limit an amount, distance or extent in which the protuberances are allowed to extend into the containers when the cover plate is applied or positioned proximal to the delivery containers thus preventing the protuberances from fully extending into the delivery containers;
    wherein at least one vent feature is provided by the stand-off height to allow at least one of a gas, a vapor, and a fluid to flow therethrough;
    and wherein the cover plate substantially prevents the escape of a lyophilizate from delivery containers during a lyophilization process;
    placing the cover plate over a plurality of syringe barrels containing a solution comprising leuprolide acetate, such that the plurality of protuberances extend at least partially into the syringe barrels;
    wherein the syringe barrels are suspended in a rack contained within a tub, wherein the rack suspends the syringe barrels in an upright position such that an opening of each of the syringe barrels faces toward a top of the tub, and wherein at least some of the plurality of extensions contact at least one of the rack and the tub;

placing the tub containing the plurality of syringes on a shelf of a lyophilizing apparatus; and lyophilizing the solution by cooling the solution and applying a vacuum to the solution.

17. The method of claim 16, wherein at least one of a gas, a vapor and a fluid are allowed to flow through the vent feature.

18. The method of claim 16, further comprising a step of examining the protuberances for the presence of lyophilizate.

19. The method of claim 16, wherein the base portion comprises four corners and the extensions are provided at each of the four corners of the base portion.

\* \* \* \* \*